United States Patent [19]

Sugarman et al.

[11] Patent Number: 4,952,373
[45] Date of Patent: Aug. 28, 1990

[54] LIQUID SHIELD FOR CARTRIDGE

[75] Inventors: Jeff Sugarman, Mountain View; Ian Harding, San Mateo; Michael Cobb, Sunnyvale, all of Calif.

[73] Assignee: Biotrack, Inc., Mountain View, Calif.

[21] Appl. No.: 341,757

[22] Filed: Apr. 21, 1989

[51] Int. Cl.$^5$ ............................................. C12M 1/20
[52] U.S. Cl. ......................................... 422/99; 422/58; 422/61; 422/73; 422/102; 422/117; 436/165; 435/291; 435/293; 435/301
[58] Field of Search .................. 422/58, 61, 68, 99, 422/102, 117, 55; 436/165; 435/287, 293, 301, 291, 808; 356/246

[56] References Cited

U.S. PATENT DOCUMENTS

| | | | |
|---|---|---|---|
| 3,127,855 | 4/1964 | Conlon | 422/99 X |
| 3,957,583 | 5/1976 | Gibson et al. | 435/287 X |
| 4,018,652 | 4/1977 | Lanham et al. | 435/287 X |
| 4,038,151 | 7/1977 | Fadler et al. | 435/287 X |
| 4,318,994 | 3/1982 | Meyer et al. | 435/301 |

Primary Examiner—Robert J. Warden
Assistant Examiner—Lynn M. Kummert
Attorney, Agent, or Firm—Leydig, Voit & Mayer

[57] ABSTRACT

A shield is provided for isolating excess liquid on the surface of a diagnostic cartridge from a monitor with which the cartridge is used. In a preferred embodiment the shield is a strip of flexible, resilient material which can lie flat while the cartridge is in its packaged condition but which automatically springs up to serve as a shielding surface when the cartridge is unpackaged and inserted into the monitor.

5 Claims, 2 Drawing Sheets

LIQUID SHIELD FOR CARTRIDGE

BACKGROUND OF THE INVENTION

1. Technical Field

This invention relates to liquid diagnostic devices and more particularly to shields for such devices to confine the excess liquid to the diagnostic devices.

2. Background

U.S. Pat. No. 4,756,884 discloses a disposable diagnostic device in the form of a cartridge which, with the use of a monitor, can be used to substantially instantly determine the prothrombin (PT) time of one's blood. Such instantaneous determination of this and other tests is of great value both to patients and to physicians in that it permits prompt diagnosis of a disease state, prescription of appropriate medication and monitoring of the proper dosage of medication, such as the oral anticoagulant coumadin commonly called Warfarin. The assignee has also developed a diagnostic device for measuring Activated Partial Thromboplastin Time (APTT). This is the subject of co-pending U.S. Application Ser. No. 341,045, filed on Apr. 20, 1989. While the present invention has broad application beyond these specific examples, these will be used throughout this application as typical applications.

Each of these devices mentioned above is roughly the size of a conventional plastic identification or "credit" card and is a single use disposable item. Both are used with suitable monitors about the size of a small to medium-sized book and having a receiving slot therein into which the cartridge is partially inserted in preparation for the measurement. Each cartridge has a liquid receiving well which remains outside the monitor and into which the liquid to be analyzed is deposited, either directly from a pricked finger or using a capillary tube, syringe, or the like.

Two related problems and disadvantages have been recognized, and the present invention has been developed to solve both of them. One problem is the occasional, inadvertent, seepage of excess liquid from the surface of the cartridge into the interior of the monitor such that a failsafe self-diagnostic system within the monitor will prevent it from reporting test results until the monitor is cleaned. Specifically, internal sensors present in the monitors for the cartridges described above, such as light sensing transducers and other instruments, can be affected by the unintentional presence of liquid, such as blood. If, when the self-diagnostic check is being run, the readings from the sensors are outside of the expected ranges, the monitor will withhold the reporting of any test results until the readings return to the normal range.

A related problem, apart from having liquid interfere with the operation of the monitor, is the contamination of the monitor which results from contact of the liquid with either the interior or exterior of the monitor. Not only is such contact unsightly and unsanitary, but the hazards of contact with infected bodily liquids of the diagnosee, and the desirability of preventing such contact, are so apparent as to require no further elaboration. Whether the contact of the excess liquid renders the monitor completely inoperative or simply contaminates the monitor, it requires removal of the monitor from service so that it can be cleaned and repaired if necessary.

The problem of confining excess liquid to the surface of cartridges such as those disclosed in the referenced patents is complicated by a series of factors. One such factor is the desirability that the device be ready to use immediately upon its removal from its packaging. Another factor is the need for space efficient nesting of the packaged cartridges to reduce storage space requirements. Yet another consideration is that the liquid shield not change or otherwise adversely affect the design or manufacture of the cartridges, which involves some ultrasonic assembly steps requiring flat cartridge surfaces. Still another consideration is the requirement that neither the liquid shield, nor any material used to attach it, impair or interfere with the accuracy of results obtained when using the cartridge with an appropriate monitor. Further, it is desirable that new shielded cartridges be usable with monitors already in the field.

SUMMARY OF THE INVENTION

The present invention provides a shield for confining liquid to be analyzed to that portion of a device, such as a cartridge surface, ortside the monitor. This shield comprises a resilient member which, in its free state, projects away from the surface of the device to a distance sufficient to assure that it covers any gap between the liquid receiving surface of the device and the monitor in order to confne excess liquid to the surface of the device and prevent it from entering the monitor. The shield may be provided with sufficient resiliency to permit it to lie flat with the cartridge in its packaged state, but to automatically project upward when the package is opened so that the device is ready for use. An attachment means is employed which does not adversely affect the operation of the monitor or accuracy of the readings.

BRIEF DESCRIPTION OF THE FIGURES

This invention will be better understood by reference to the following detailed description of specific embodiments when considered in combination with the drawings that form part of this specification, wherein.

DETAILED DESCRIPTION OF SPECIFIC EMBODIMENTS

The present invention provides a liquid shield particularly suited for use with liquid diagnostic devices which receive liquid at one surface and are used in connection with other equipment, such as a monitor. One example of such a liquid diagnostic device is one for determining the prothrombin time of one's blood by first applying a drop of blood to a well in the cartridge. The blood then automatically flows into a chamber containing reagent and continues traveling through a serpentine capillary path until sufficient clotting occur; that the capillary travel stops. U.S. Pat. No. 4,756,884, incorporated herein by reference, discloses such a cartridge. Another cartridge designed for a different analysis but which is employed in a generally similar manner with a monitor of the same general configuration is disclosed in the aforementioned co-pending U.S. Pat. Application Ser. No. 341,045, filed on Apr. 20, 1989, incorporated herein by reference.

Figure 1:
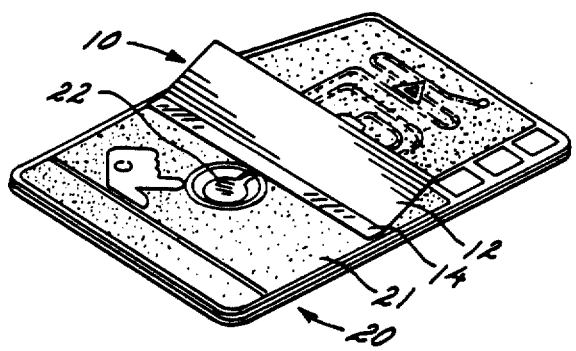
FIG. 1 is a perspective view of a liquid diagnostic cartridge with a liquid shield according to the present invention applied thereto.
Figure 2:
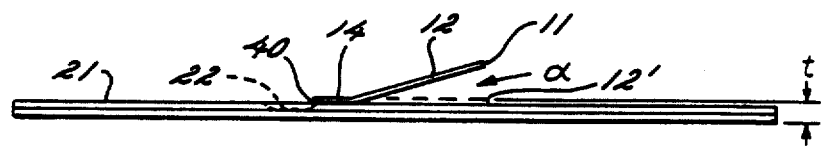
FIG. 2 is a side view of the cartridge and liquid shield of FIG. 1.

Referring jointly to FIGS. 1 and 2, a liquid shield device 10 according to the present invention is shown affixed to the top surface of a cartridge 20. The solid lines in FIG. 2 show the liquid shield 10 in its free state, that is, with no external forces applied thereto. The dotted lines show the liquid shield 10 deflected against the upper surface 21 of the cartridge, as when packaged, discussed below.

Figure 3:
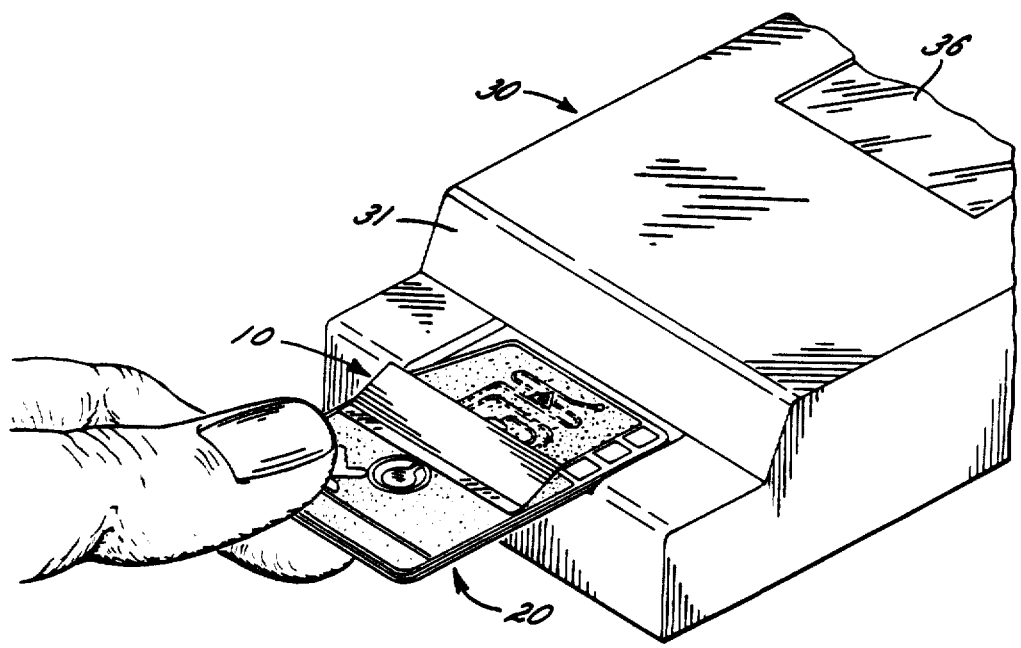
FIG. 3 is a perspective view of the cartridge and liquid shield of FIG. 1 being inserted into a monitor.
Figure 4:
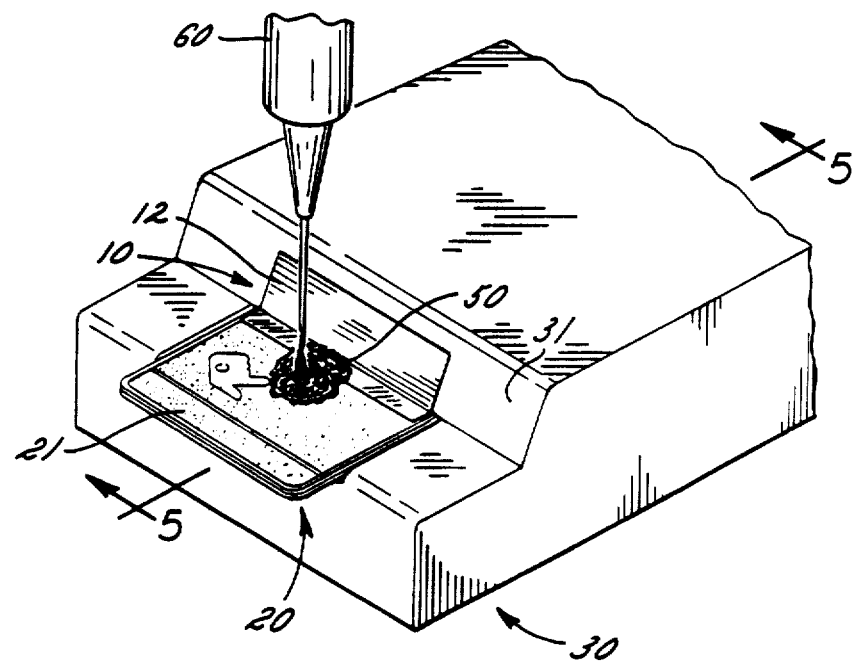
FIG. 4 is a perspective view of the cartridge and liquid shield of FIG. 1 fully inserted into the monitor and receiving an excess amount of liquid from a syringe.

In the free state shown in FIGS. 1 and 2, the leading edge 11 of the liquid shield 10 projects upward from the otherwise substantially flat upper surface 21 of the cartridge. The shield is shown mounted to the cartridge substantially transverse thereto at a location between a liquid receiving well 22 and the ultimate location of the monitor surface to be shielded with the cartridge in its installed condition. This location is illustrated in FIGS. 3 and 4. This arrangement allows the shield 10 to accomplish the desired confining of the liquid to the cartridge surface and shielding of the monitor surface 31 from contact by the liquid. By fabricating the shield from a resilient material, such as a thin plastic or metallic film, the shield may be attached to the cartridge at a location sufficiently far back from the monitor surface 31 to avoid interference by the shield when the leading portion of the cartridge is inserted and seated into position in the monitor. In this regard it will be appreciated that the upstanding "flap" 12 of the shield 10 may be positioned to engage and ride up the monitor surface 31 as the cartridge 20 is inserted into the monitor. This arrangement assures that the shield is rendered unobtrusive while the cartridge is in place in the monitor. An additional advantage of this arrangement, especially when the shield is made of a substantially opaque material, is that the shield can serve an auxiliary purpose of preventing the entry of light into any gap 32 between the cartridge surface 21 and the monitor surface 31 which might otherwise impair the functioning of any light-sensitive instruments or transducers (shown generally at 34) within the monitor. A further advantage of making the shield from an opaque material is that the orientation of the flap 12 of the liquid shield can also be passively verified by even the monitors presently in the field. The manner in which this is accomplished can be appreciated by reference to FIG. 4.

In the event the flap portion 12 of the liquid shield 10 should enter the gap 32, as indicated by the dotted lines 12', it will be interposed between a light source and sensor (shown schematically at 34 and 35), and will indicate a malfunction. Inasmuch as the monitors in the field already employ a self-diagnostic program which displays alpha/numeric messages at readout 36 the program may readily be supplemented to include an appropriate message to indicate that the light path has been blocked. This message could prompt the user to remove the cartridge and either reinsert it correctly or substitute another cartridge.

It will be appreciated that, in the interest of efficient packing and storage, it is highly desirable that the liquid shield 10 not significantly increase the effective packing thickness "t" of the cartridge. To this end, by making the liquid shield of a sufficiently resilient material, such as a thin plastic film, it may be readily flattened against the cartridge as shown in FIG. 2A. Materials considered suitable for the liquid shield are films of polysulfone, polyester, cellulose acetate, polycarbonate, polyetheretherketone, polymethylpentene, polyetherimide, polyethersulfone, polyvinylidene fluoride, metal foils, reinforced papers and laminates of these materials.

The angle $\alpha$ which the flap 12 makes with the surface 21 of the cartridge 20 may range between the minimum required to assure that the flap does not enter the gap 32 and the angle of inclination of the monitor surface 31. Specifically, angles of between about 10° and 45° may be suitable, with the preferred range for the cartridge and monitor shown being between about 25° and 35°.

The thickness of the material can vary so long as the shield accomplishes the desired functions as set forth above. Depending on the specific material selected, films as thin as a couple thousandths of an inch may be satisfactory. A 0.004" thick polysulfone film, heat-formed to have an angle $\alpha$ of approximately 25° between the portion 14 of the shield fastened to the cartridge and upstanding flap 12, has been found to work highly satisfactorily.

The manner in which the portion 14 of the liquid shield 10 is attached to the surface 21 of the cartridge 20 is important from several standpoints. First, the shield must remain firmly attached throughout its shelf life, during most of which time it may be sealed within a foil or similar pouch. Secondly, the shield itself, and any adhesive material (shown in the drawings as item 40) which is used to attach the shield to the cartridge, must not adversely affect the operation of the cartridge. Specifically in this regard, any such adhesive must not release such quantities of vapors incompatible with the remainder of the cartridges, or the reagents coated on the internal surfaces thereof, as might ultimately impair the functioning or accuracy of the results obtained using the cartridge. An adhesive which has been found to be suitable in attaching a polysulfone liquid shield to a cartridge molded from acrylonitrile-butadiene-styrene (ABS) resin is 3M 966. Other acrylic and rubber based adhesives have been shown to be suitable. Ultrasonic welding and heat sealing may also be suitable alternatives which avoid the use of separate adhesives entirely.

Figure 5:
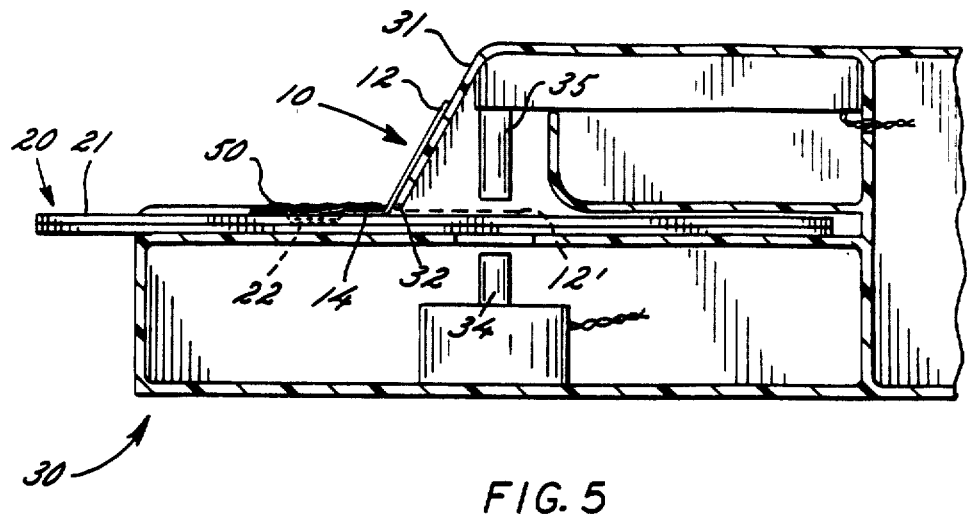
FIG. 5 is a partial sectional view of the cartridge, liquid shield and monitor of FIG. 4 taken along line 5—5.

The operation of the liquid shield is considered to be apparent from the foregoing discussion. Briefly explaining it with specific reference to FIGS. 4 and 5, however, liquid may be added to the well 22 of the cartridge 20 directly from a pricked finger, or using any other conventional means, such as a capillary tube or syringe (depicted in FIG. 4 as item 60). Under normal circumstances a single drop or two of the liquid is sufficient for the analysis and will be readily contained in the well. Under these conditions, the liquid shield 10 will be unnecessary to block liquid although, as discussed above, it may still fulfill a useful light-blocking function. In the event excess liquid is introduced onto the surface of the cartridge, as indicated at 50 in FIGS. 4 and 5, the possibility exists that, without the liquid shield of the present invention, the liquid might reach the surface 31 of the monitor, and/or enter the gap 32. It must be recognized that the embodiment of the liquid shield shown in the figures will not be effective against a "flood" of a great excess of liquid. It will, nevertheless, be effective in the vast majority of instances where there is a moderate excess of liquid, or where an otherwise proper amount of liquid is errantly applied.

From the above discussion, it will be appreciated that there is described a liquid shield for use with diagnostic cartridges which can be applied to cartridges of existing design without necessitating any changes to the basic cartridge manufacture, or the design or manufacture of the monitors designed for use with the cartridges.

The invention now being fully described, it will be apparent to one of ordinary skill in the art that many changes and modifications can be made thereto without departing from the spirit or scope of the appended claims.

We claim as our invention:

1. In combination a liquid diagnostic cartridge for use with liquids and a liquid shield, the liquid diagnostic cartridge comprising a first portion for insertion into a monitor and a second portion having a liquid receiving well in one surface thereof, the liquid shield being attached to the one surface of the cartridge at a location between the first and second portions of the cartridge, the liquid shield comprising a resilient flap which, in a free state, stands away from the surface but which will flex into close proximity to the surface of the cartridge in response to the application of a force normal to the surface of the cartridge, whereby the shield serves to isolate liquid applied to the first portion of the cartridge from the second portion of the cartridge when unrestrained, yet deflects to minimize the overall thickness of the cartridge and shield, as when packaged.

2. The combination of claim 1 wherein the flap, when unrestrained, stands away from the surface of the diagnostic device at an angle of between about 10° and 45°.

3. The combination of claim 1 wherein the shield is fabricated from an opaque plastic film.

4. The combination of claim 1 wherein the liquid shield is fabricated from a polysulfone film.

5. The combination of claim 1 wherein the shield is fabricated from a polyester film.

* * * * *